US00PP08162P

United States Patent [19]

Keen

[11] Patent Number: Plant 8,162

[45] Date of Patent: Feb. 23, 1993

[54] MIDLAWN BERMUDAGRASS

[75] Inventor: Ray A. Keen, Manhattan, Kans.

[73] Assignee: Kansas State University Research Foundation, Manhattan, Kans.

[21] Appl. No.: 706,273

[22] Filed: May 28, 1991

[51] Int. Cl.[5] ..... A01H 5/00

[52] U.S. Cl. ..... Plt./90

[58] Field of Search ..... Plt./89, 90

*Primary Examiner*—James R. Feyrer

*Attorney, Agent, or Firm*—Hovey, Williams, Timmons & Collins

[57] ABSTRACT

A triploid variety of Bermudagrass called Midlawn, produces no viable seed, has superior cold hardiness, excellent turf quality, with fine texture, dark green color, good sod density and is slower spreading than Midiron and other, similar turf type Bermudagrass.

4 Drawing Sheets

BACKGROUND OF THE INVENTION

The present invention relates to a new and distinct variety of hybrid Bermudagrass which is well-adapted to the transition zone of the United States. This turf-type hybrid was developed by open-pollination at the Kansas State University polycross nursery in Fort Hayes, Kans.

Bermudagrass is widely grown as a lawn grass, forage plant and for erosion control. Common Bermudagrass requires warm weather for growth. The devastating winter of 1989–90 killed many acres of Bermudagrass, establishing a need for hardy selections possessing high turf quality, particularly in the northern Bermudagrass belt or transition zone. In addition, current commercial Bermudagrass cultivars present certain problems for home lawn use in that they tend to be aggressive and of a coarse texture.

The distinguishing characteristics of this new variety of plant are excellent cold hardiness combined with high turf quality, that is to say, fine texture, dark green color, and good sod density. Midlawn Bermudagrass possesses increased cold tolerance to −20° F. and is also very drought resistant. This cultivar has a shorter internode length, which advantageously makes it less aggressive and more suitable for residential use while at the same time providing a greater density to Midlawn turf. The lack of aggressiveness makes this a desirable grass for use around other ornamental plants. The average internode length of field grown Midlawn plants measures about 43 mm, while the average internode length of field grown Midiron Bermudagrass is about 51 mm.

Midlawn Bermudagrass is a clone, vegetatively propagated from rhizomes or stolons. The cultivar originated from a single seedling and was vegetatively propagated at Manhattan, Kans. The seed parent of Midlawn was a cold hardy, common tetraploid ($2n=4\times=36$) Bermudagrass *Cynodon dactylon* var. *dactylon* collected from the campus of the Michigan State University of East Lansing. The pollen parent was one of several African diploid ($2n=2\times=18$) Bermudagrasses *C. transvaalensis*, growing in the same polycross nursery as the common parent. Midlawn is a triploid with $2n=3\times=27$ chromosomes and is highly male and female sterile. The clone progeny have been shown to be stable in all distinguishing characteristics.

BRIEF DESCRIPTION OF THE DRAWING FIGURES

BOTANICAL DESCRIPTION OF THE PLANT

Figure 1:
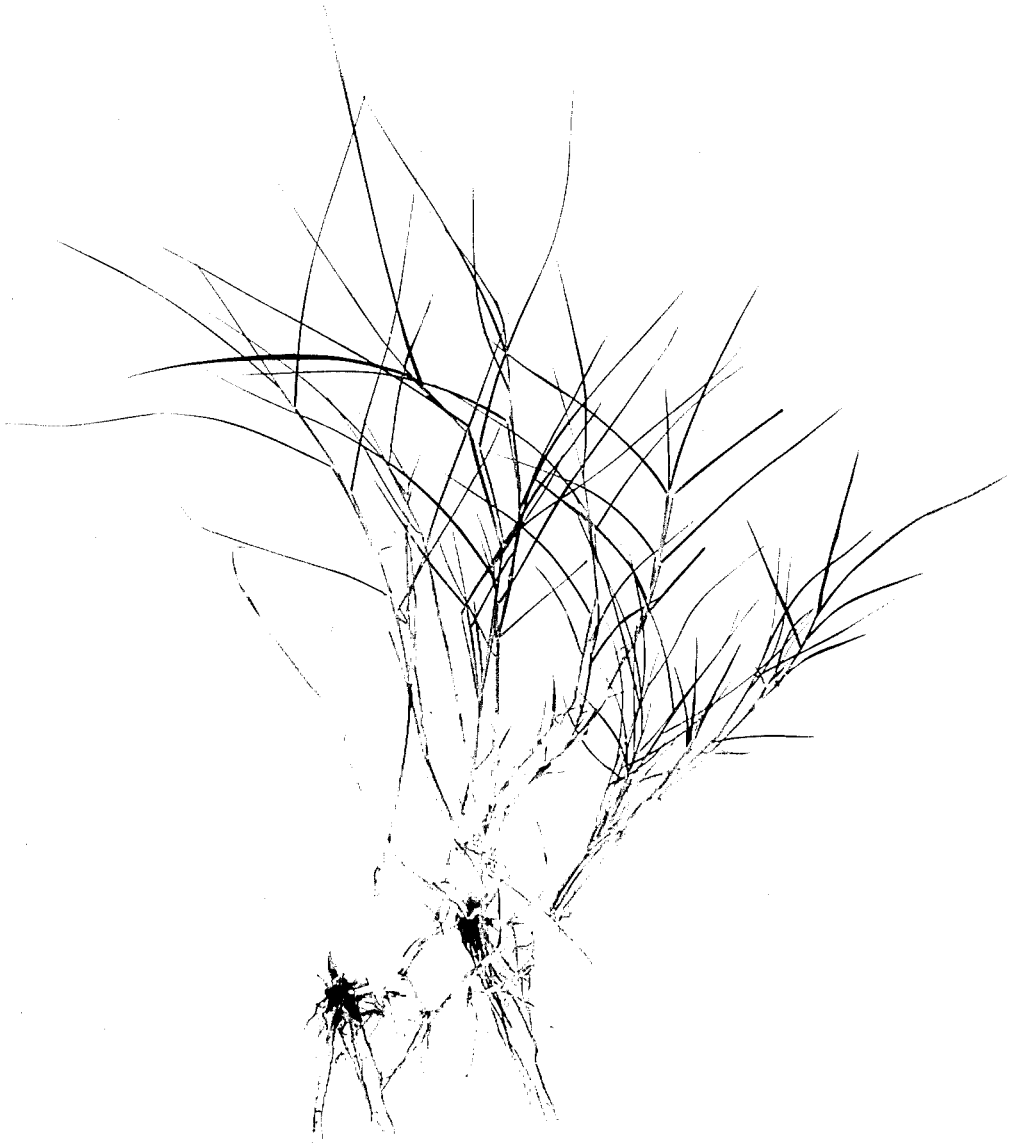
FIG. 1 is a color photographic representation of a nursery grown potted Midlawn Bermudagrass plant in accordance with the invention.
Figure 2:
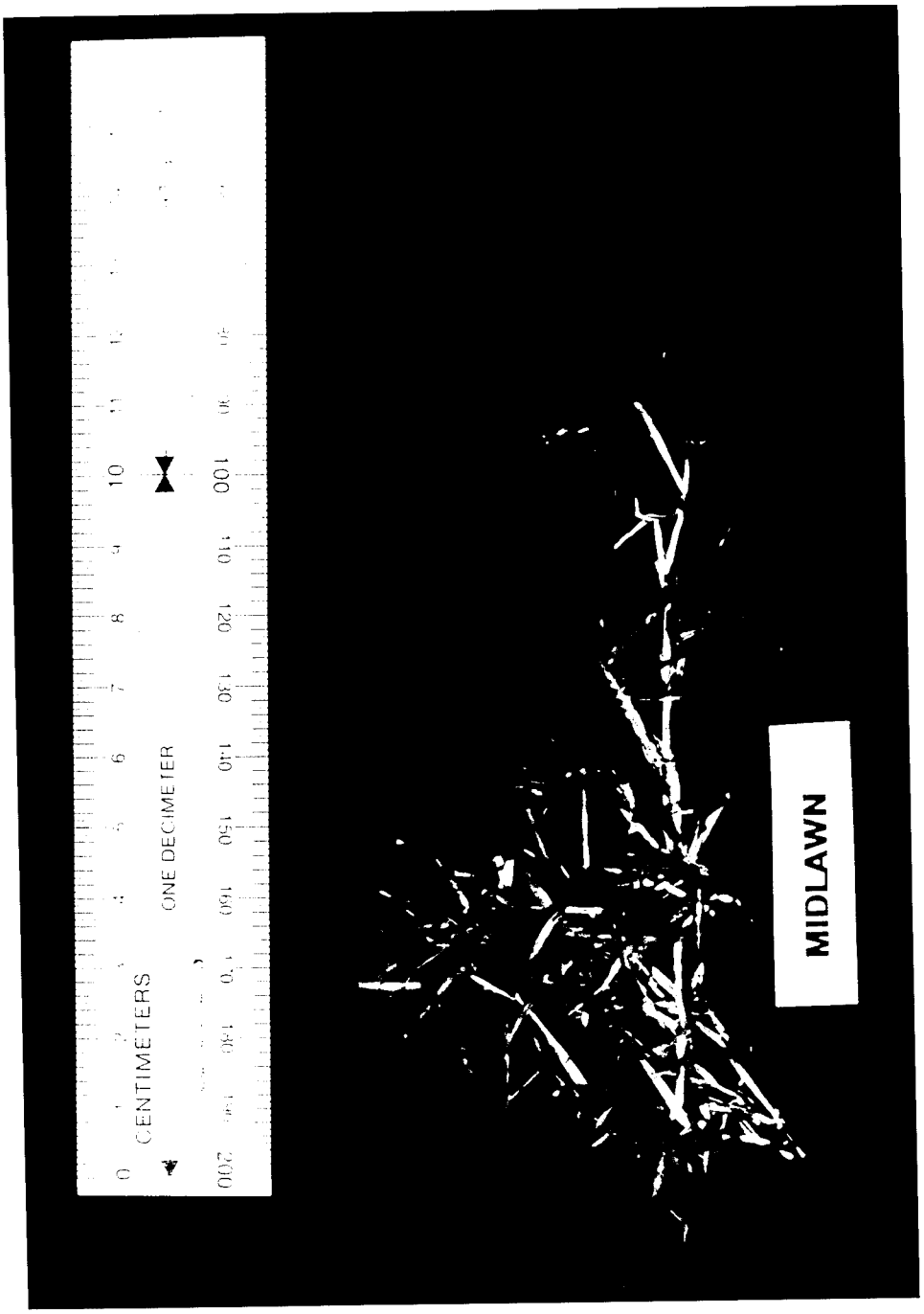
FIG. 2 is a color photographic representation of a field grown Midlawn Bermudagrass plant subject to periodic mowing.

The following taxonomic description is of the plant when grown in the greenhouse as a potted plant and describes specimens cultured under controlled conditions which can be reproduced. However, the description to follow should not be construed as limiting with regard to the expressed characteristics of this plant, because the characteristics of 'Midlawn' have been observed to vary widely as a function of stage of growth, growing conditions, geographic location of culture, and management practices to which sod of the plant is subjected. Such differences in appearance of this plant can be appreciated with a comparison of FIG. 1 and FIG. 2 of the drawing, for example.

MIDLAWN BERMUDAGRASS

'Midlawn' Bermudagrass, *Cynodon dactylon*×*Cynodon transvaalensis*, is a stononiferous sward-forming perennial with dense, slender underground tan to light brown rhizones; surface stolons slender, prostrate, and slow spreading; culms slender, about 5–30 cm high and about 0.5–1.5 mm in diameter in greenhouse grown, potted plants. Leaf-blades flat, or folded when dry, often short and narrow, about 1.5–2.5 mm wide and 70–85 mm long on fully extended mature shoots; leaves dark green with scattered hairs on upper (adaxial) surface; ligule a membranmous rim about 0.2–0.3 mm long, ciliate on the edge; leaf sheaths light green, sometimes developing purple (anthocyanin) pigmentation at base, glabrous except for few hairs at base, about 10–40 mm in length and about 1-5 mm in width. Internodes light green, sometimes developing purple (anthocyanin) pigmentation. Inflorescences infrequent, seldom producing seed heads; no viable seed produced. Midlawn exhibits a dark fern leaf color, #21-G-8, Maerz et al., *A Dictionary of Color,* McGraw-Hill Book Company, Inc. 2 Ed. (1950). Growth habit decumbent, prostrate, with a maximum height less than about 6 inches (15.24 cm).

Midlawn is effectively sterile but does exhibit complete flower parts. Anthers are formed in the flowers; however, little if any viable pollen is formed within the anthers.

Unmowed midlawn exhibits an average internode length from about 39.4 to 45.7 mm, and roots readily form at each node under favorable conditions of soil moisture and temperature.

Midlawn has been experimentally tested in comparison to other turf Bermudagrass cultivars at several locations in the United States for overall turf performance. It is superior to commercial turf Bermudagrass varieties in one or more of the following characteristics affecting turf performance: fineness of texture, sod density, color, and cold tolerance. Midlawn showed the highest frost tolerance rating of 28 cultivars tested, including Midiron. As compared with other seedless types, Midlawn produces fewer seed heads, and is less aggressive. Midlawn has a growth rate comparable to Tifgreen Bermudagrass which is the most widely used of Bermudagrass cultivars in the southern and southeastern parts of the United States. It is anticipated that Midlawn will be used exclusively as a lawn grass and for recreational turfs; it is not anticipated that Midlawn will be used as a forage grass. Midlawn exhibits substantially mowing and thatching characteristics as compared with conventional Bermudagrass cultivars.

Figure 3:
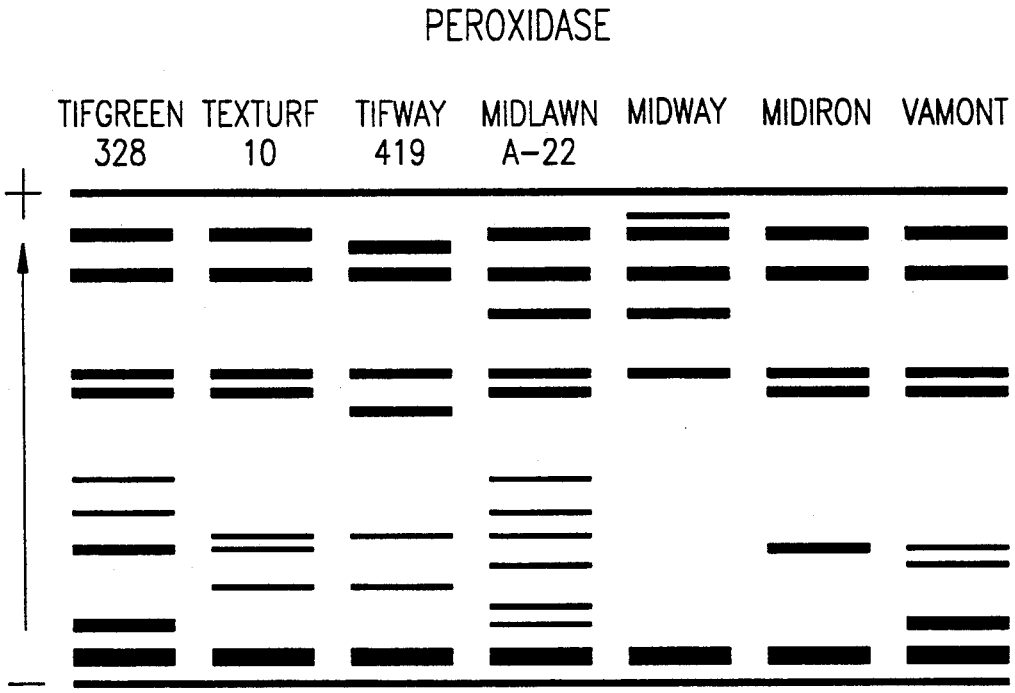
FIG. 3 is a graphic representation of electrophoretic banding patterns in the peroxidase isoenzyme system.
Figure 4:
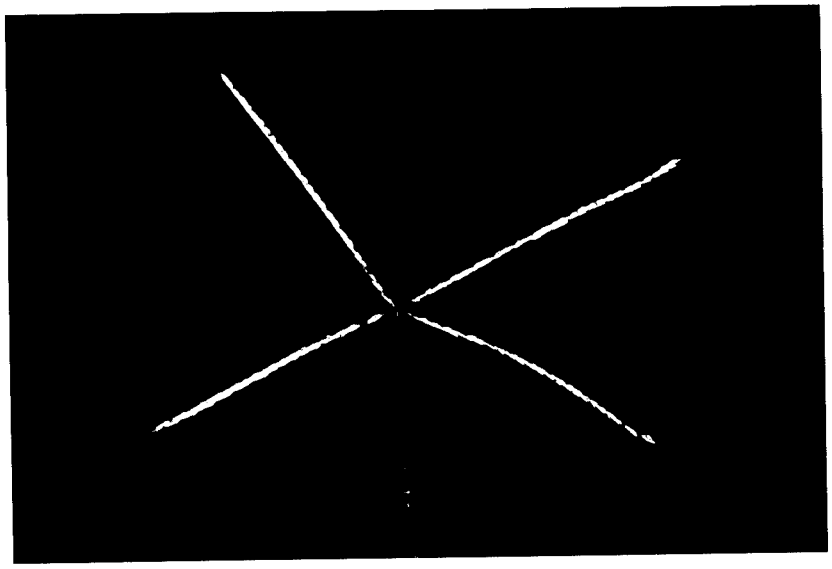
FIG. 4 is a phogograph illustrating the inflorescence of Midlawn Bermudagrass.
Figure 5:
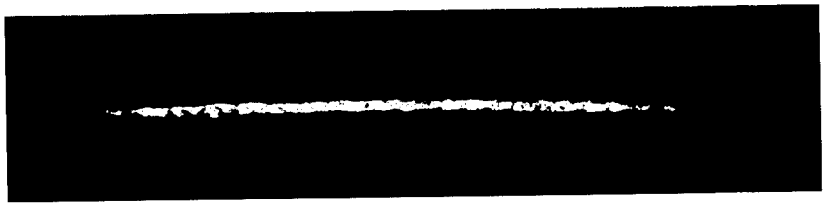
FIG. 5 is a photograph illustrating a single receme of Midlawn Bermudagrass.
Figure 6:
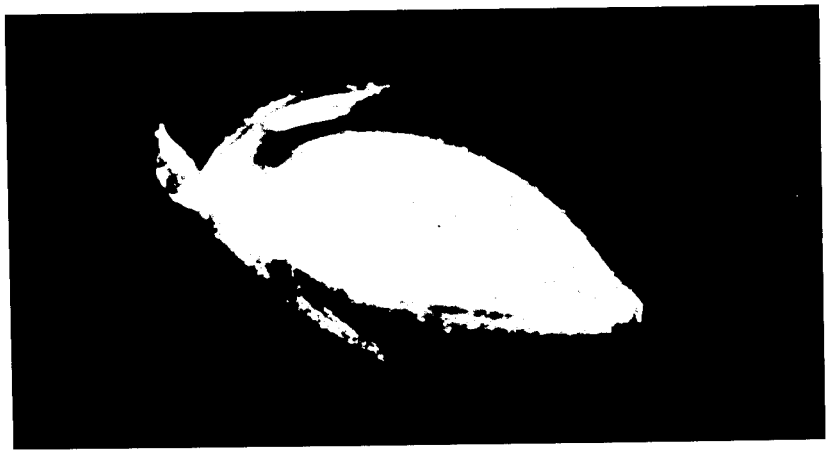
FIG. 6 is a photograph illustrating a single spikelet of Midlawn Bermudagrass.

Midlawn Bermudagrass is genetically and physiologically distinctive as compared to other turf Bermudagrass cultivars. As best shown in FIG. 3, Midlawn presents distinct electrophoretic banding patterns in the peroxidase isoenzyme system. Moreover, Midlawn exhibits inflorescence of unilateral racemes numbering 3-6, usually 4, 3-6 cm long (average 4.0 cm); spikelets perfect, 2-2.5 mm long with medium spacing on raceme, about 2.5 mm; glumes lancelate in side view, 1-nerved, the upper ⅓-½ as long as the spikelet; lemma pubescent on the keel; palea glaborus.

The outstanding characteristics of this new variety of Bermudagrass are greater cold-tolerance combined with excellent turf quality. Midlawn is a slow growing, fine textured dark green home lawn type grass with good density, few seed heads, and good sod strength.

The following tables 1-9 further describe the characteristics of Midlawn (A-22), as compared with other cultivars. Tables 3 and 4 confirm the spring green-up and frost heartiness of Midlawn. Table 9 demonstrates that Midlawn is resistant to Spring Dead Spot (*Ophiosphaerella herpotrica*).

TABLE 1

Sod Quality of Bermudagrass Clones, 1987-88[1]

| Bermuda clone | Internode length (in.) | Rhizome depth | Sod strength (lbs.) 1978 | 1981 | (kgs) 1988 |
|---|---|---|---|---|---|
| Midiron | 2.0 | 1.75 | 12.5 | 17.7 | 16.7 |
| KS Improved | 1.5 | 4.28 | 28.0 | 23.2 | NA |
| Midfield | 1.8 | 2.72 | 33.5 | 44.9 | 45.7 |

TABLE 1-continued

Sod Quality of Bermudagrass Clones, 1987-88[1]

| Bermuda clone | Internode length (in.) | Rhizome depth | Sod strength (lbs.) 1978 | 1981 | (kgs) 1988 |
|---|---|---|---|---|---|
| Midlawn | 1.7 | 2.34 | 34.3 | 31.8 | 30.7 |

[1]Data for 1978 and 1981 from Kansas State University Research Center; 1988 data from Mississippi State University

TABLE 2

Mean Turfgrass Quality Ratings of Bermudagrass Cultivars at Thirteen Locations in the United States, 1990[1]

| Bermuda clone | Turfgrass Quality Ratings (1-9, 9 = ideal turf) AR | AZ | CA2 | CA3 | FL | KS | LA |
|---|---|---|---|---|---|---|---|
| Tifway | 7.9 | 7.9 | 6.7 | 6.4 | 7.9 | 1.0 | 7.6 |
| Tifway II | 7.8 | 7.8 | 6.4 | 6.4 | 8.1 | 1.5 | 7.7 |
| MSB-10 | 7.6 | 1.8 | 6.9 | 6.3 | 8.1 | 1.7 | 7.7 |
| A-29 | 7.1 | 6.9 | 5.5 | 5.5 | 6.4 | 8.2 | 7.1 |
| Midfield (E-29) | 7.0 | 6.4 | 5.6 | 5.7 | 6.6 | 8.0 | 6.2 |
| Midiron | 6.8 | 6.4 | 5.9 | 5.8 | 6.9 | 7.5 | 6.8 |
| Midlawn (A-22) | 7.1 | 6.6 | 5.5 | 5.9 | 5.9 | 7.7 | 6.6 |
| MSB-20 | 7.4 | 7.1 | 5.7 | 5.5 | 7.7 | 1.0 | 7.1 |
| NM 43 | 6.9 | 7.1 | 5.6 | 5.8 | 7.7 | 1.2 | 7.2 |
| MSB-30 | 6.0 | 6.9 | 6.5 | 5.8 | 6.5 | 2.7 | 7.1 |
| Tufcote | 7.6 | 6.2 | 5.7 | 5.7 | 7.2 | 2.0 | 7.4 |
| Tifgreen | 6.7 | 6.9 | 5.7 | 5.6 | 8.1 | 1.3 | 6.8 |
| CT-23 | 5.0 | 7.2 | 5.6 | 5.9 | 6.5 | 3.0 | 7.2 |
| NM 507 | 6.3 | 7.7 | 6.2 | 5.6 | 8.1 | 1.0 | 7.4 |
| Texturf 10 | 6.3 | 6.6 | 5.5 | 5.5 | 7.0 | 2.8 | 6.3 |
| NM 471 | 5.8 | 6.9 | 6.1 | 6.0 | 7.6 | 1.0 | 7.3 |
| RS-1 | 6.0 | 5.6 | 5.5 | 5.7 | 5.7 | 5.8 | 5.9 |
| FB-119 | 5.4 | 6.1 | 5.4 | 5.2 | 6.7 | 1.0 | 7.3 |
| NM 375 | 5.7 | 6.2 | 5.4 | 5.6 | 7.1 | 1.0 | 6.6 |
| Vamont | 5.5 | 5.4 | 5.2 | 5.3 | 6.7 | 3.2 | 5.7 |
| NMS 3 | 4.7 | 6.4 | 5.3 | 5.5 | 6.7 | 1.0 | 6.8 |
| NM 72 | 4.8 | 6.4 | 5.2 | 5.1 | 7.8 | 1.0 | 6.6 |
| NMS 4 | 5.6 | 6.3 | 5.5 | 5.3 | 7.2 | 1.0 | 6.2 |
| Guymon | 5.1 | 6.2 | 4.6 | 5.2 | 6.2 | 6.2 | 5.6 |
| Numex-Sahara | 4.7 | 4.7 | 5.2 | 5.1 | 4.9 | 1.0 | 6.3 |
| NMS 2 | 4.9 | 4.5 | 5.1 | 5.1 | 3.8 | 1.0 | 5.4 |
| NMS 14 | 4.5 | 4.6 | 4.9 | 4.8 | 4.6 | 1.0 | 5.2 |
| AZ Common | 4.6 | 4.2 | 4.8 | 4.9 | 4.4 | 1.0 | 5.4 |
| LSD VALUE | 1.1 | 0.6 | 0.4 | 0.4 | 1.1 | 1.4 | 0.6 |

| Bermuda clone | Turfgrass Quality Ratings (1-9, 9 = ideal turf) MD | MO | MS | UB | VA1 | VA4 | Mean |
|---|---|---|---|---|---|---|---|
| Tifway | 7.1 | 1.9 | 7.5 | 7.3 | 6.2 | 7.1 | 6.3 |
| Tifway II | 6.8 | 1.0 | 7.7 | 7.3 | 6.3 | 7.1 | 6.3 |
| MSB-10 | 6.8 | 1.0 | 7.6 | 6.7 | 6.3 | 6.8 | 6.3 |
| A-29 | 5.8 | 1.4 | 5.1 | 7.0 | 7.0 | 5.5 | 6.0 |
| Midfield (E-29) | 5.8 | 2.8 | 4.4 | 6.8 | 6.5 | 5.9 | 6.0 |
| Midiron | 5.3 | 2.7 | 4.2 | 6.3 | 6.2 | 5.8 | 5.9 |
| Midlawn (A-22) | 5.7 | 1.4 | 5.1 | 6.7 | 6.2 | 5.8 | 5.8 |
| MSB-20 | 6.3 | 1.0 | 6.9 | 7.6 | 5.5 | 6.6 | 5.8 |
| NM 43 | 6.2 | 1.0 | 6.7 | 7.7 | 6.2 | 6.1 | 5.8 |
| MSB-30 | 6.7 | 1.5 | 5.9 | 6.2 | 5.7 | 7.1 | 5.7 |
| Tufcote | 5.4 | 1.0 | 5.6 | 7.4 | 6.5 | 6.7 | 5.7 |
| Tifgreen | 5.9 | 1.0 | 6.2 | 7.8 | 6.0 | 6.4 | 5.7 |
| CT-23 | 6.4 | 1.0 | 5.6 | 5.7 | 4.8 | 6.2 | 5.4 |
| NM 507 | 6.2 | 1.0 | 4.5 | 4.3 | 4.8 | 6.9 | 5.4 |
| Texturf 10 | 5.5 | 1.0 | 4.7 | 5.8 | 6.3 | 6.3 | 5.4 |
| NM 471 | 5.8 | 1.0 | 4.4 | 4.8 | 5.2 | 6.9 | 5.3 |
| RS-1 | 5.3 | 1.5 | 3.7 | 5.8 | 5.7 | 5.6 | 5.2 |
| FB-119 | 5.8 | 1.2 | 4.6 | 6.3 | 6.3 | 6.0 | 5.2 |
| NM 375 | 5.2 | 1.0 | 4.0 | 6.1 | 5.8 | 6.0 | 5.1 |
| Vamont | 4.8 | 2.1 | 4.0 | 4.9 | 5.7 | 5.8 | 5.0 |
| NMS 3 | 5.7 | 1.0 | 3.8 | 5.9 | 5.5 | 6.2 | 5.0 |
| NM 72 | 5.4 | 1.0 | 4.5 | 5.4 | 4.8 | 6.2 | 4.9 |
| NMS 4 | 5.1 | 1.2 | 2.7 | 5.8 | 5.0 | 5.9 | 4.8 |
| Guymon | 4.8 | 2.6 | 2.2 | 5.1 | 3.2 | 3.0 | 4.6 |
| Numex-Sahara | 5.2 | 1.0 | 2.6 | 5.2 | 4.0 | 5.6 | 4.3 |
| NMS 2 | 5.3 | 1.0 | 2.4 | 5.4 | 3.8 | 5.4 | 4.1 |
| NMS 14 | 4.6 | 1.0 | 2.3 | 4.9 | 4.2 | 5.1 | 4.0 |
| AZ Common | 3.4 | 1.0 | 2.2 | 5.0 | 4.0 | 4.7 | 3.8 |

TABLE 2-continued

Mean Turfgrass Quality Ratings of Bermudagrass Cultivars at Thirteen Locations in the United States, 1990[1]

| | | | | | | | |
|---|---|---|---|---|---|---|---|
| LSD VALUE | 1.1 | 1.1 | 0.7 | 0.8 | 1.6 | 0.7 | 0.3 |

[1]In certain states tests were performed at more than one location, hence CA2 and CA3 for California and VA1 and VA4 for Virginia.
To determine statistical differences among entries, subtract one entry's mean from another. Statistical differences occur when this value is larger than the corresponding LSD value (LSD 0.05).

TABLE 3

Spring Greenup Rating of Bermudagrass Cultivars, 1990[1]

| | Greenup Ratings (1–9, 9 = completely green) | | | | |
|---|---|---|---|---|---|
| Bermuda clone | AR | AZ | FL | MS | Mean |
| MSB-20 | 5.7 | 6.0 | 5.3 | 5.7 | 5.7 |
| Midfield (E-29) | 6.0 | 6.3 | 5.0 | 4.0 | 5.3 |
| NM 43 | 5.3 | 6.3 | 4.3 | 5.0 | 5.3 |
| Midlawn (A-22) | 5.7 | 7.0 | 3.3 | 4.7 | 5.2 |
| Tifway | 5.0 | 6.3 | 4.3 | 5.0 | 5.2 |
| Vamont | 5.0 | 6.0 | 4.7 | 4.7 | 5.1 |
| MSB-10 | 3.7 | 6.0 | 5.0 | 5.0 | 4.9 |
| Midron | 5.3 | 6.3 | 2.7 | 5.0 | 4.8 |
| Tufote | 5.7 | 4.7 | 3.0 | 5.7 | 4.8 |
| Tifgreen | 5.0 | 5.3 | 4.3 | 4.3 | 4.8 |
| Tifway II | 4.0 | 5.0 | 4.7 | 5.0 | 4.7 |
| Texturf 10 | 3.7 | 6.3 | 4.0 | 4.0 | 4.5 |
| A-29 | 4.7 | 5.0 | 3.3 | 4.7 | 4.4 |
| RS-1 | 5.7 | 5.0 | 2.7 | 4.0 | 4.3 |
| FB-119 | 1.7 | 6.7 | 5.7 | 3.0 | 4.3 |
| NM 507 | 2.0 | 6.7 | 4.3 | 3.7 | 4.2 |
| Guymon | 5.7 | 5.0 | 3.3 | 2.0 | 4.0 |
| NM 375 | 2.7 | 5.7 | 4.0 | 3.3 | 3.9 |
| NM 72 | 2.0 | 5.3 | 4.3 | 4.0 | 3.9 |
| MSB-30 | 1.7 | 7.3 | 2.3 | 4.0 | 3.8 |
| NM 471 | 2.0 | 6.0 | 3.7 | 3.3 | 3.8 |
| AZ Common | 2.7 | 5.0 | 5.0 | 2.0 | 3.7 |
| NMS 4 | 2.3 | 5.3 | 2.7 | 2.3 | 3.2 |
| Numex-Sahara | 3.0 | 4.3 | 3.0 | 2.0 | 3.1 |
| NMS 14 | 2.7 | 4.7 | 2.3 | 2.0 | 2.9 |
| CT-23 | 1.0 | 4.7 | 1.3 | 3.0 | 2.5 |
| NMS 2 | 3.0 | 3.7 | 1.3 | 2.0 | 2.5 |
| NMS 3 | 1.3 | 3.7 | 2.0 | 2.3 | 2.3 |
| LSD VALUE | 1.3 | 1.4 | 1.5 | 1.0 | 0.6 |

[1]To determine statistical differences among entries, subtract one entry's mean from another. Statistical differences occur when this value is larger than the corresponding LSD value (LSD 0.05).

TABLE 4

Frost Tolerance Ratings of Bermudagrass Cultivars, 1990[1]

| | Frost Tolerance Ratings (1–9, 9 = no injury) | | |
|---|---|---|---|
| Bermuda clone | AR | VA | Mean |
| Tifway II | 9.0 | 7.3 | 8.2 |
| Tufcote | 8.7 | 6.7 | 7.7 |
| Tifway | 8.7 | 6.3 | 7.5 |
| CT-23 | 7.7 | 7.0 | 7.3 |
| MSB-10 | 9.0 | 5.0 | 7.0 |
| Midlawn (A-22) | 8.0 | 5.3 | 6.7 |
| Midfield (E-29) | 7.3 | 5.7 | 6.5 |
| MSB-30 | 8.7 | 4.0 | 6.3 |
| NM 375 | 4.7 | 7.7 | 6.2 |
| NM 507 | 7.0 | 4.7 | 5.8 |
| A-29 | 8.0 | 3.0 | 5.5 |
| NM 471 | 7.3 | 3.7 | 5.5 |
| FB-119 | 5.3 | 5.0 | 5.2 |
| NMS 2 | 5.3 | 4.7 | 5.0 |
| NMS 4 | 6.3 | 3.7 | 5.0 |
| Texturf 10 | 6.7 | 3.3 | 5.0 |
| AZ Common | 6.7 | 3.0 | 4.8 |
| NMS 3 | 5.7 | 4.0 | 4.8 |
| Numex-Sahara | 5.3 | 4.3 | 4.8 |
| NMS 14 | 5.0 | 3.7 | 4.3 |
| RS-1 | 5.0 | 3.3 | 4.2 |
| Midiron | 5.0 | 3.0 | 4.0 |
| NM 72 | 4.3 | 3.7 | 4.0 |
| Tifgreen | 5.7 | 2.3 | 4.0 |
| Vamont | 2.7 | 5.3 | 4.0 |
| Guymon | 4.7 | 3.0 | 3.8 |
| NM 43 | 5.0 | 2.3 | 3.7 |

TABLE 4-continued

Frost Tolerance Ratings of Bermudagrass Cultivars, 1990[1]

| | Frost Tolerance Ratings (1–9, 9 = no injury) | | |
|---|---|---|---|
| Bermuda clone | AR | VA | Mean |
| MSB-20 | 5.0 | 2.0 | 3.5 |
| LSD VALUE | 1.5 | 1.3 | 1.0 |

[1]To determine statistical differences among entries, subtract one entry's mean from another. Statistical differences occur when this value is larger than the corresponding LSD value (LSD 0.05).

TABLE 5

Winter Kill Rating of Bermudagrass Cultivars, 1990[1]

| | Percent Winter Kill: Locations | | | |
|---|---|---|---|---|
| Bermuda clone | IL | MO | UB | Mean |
| NM 507 | 99.0 | 99.0 | 84.7 | 94.2 |
| NM 471 | 99.0 | 99.0 | 81.7 | 93.2 |
| C1-23 | 99.0 | 99.0 | 80.0 | 92.7 |
| NMS 14 | 99.0 | 99.0 | 73.3 | 90.4 |
| AZ-Common | 99.0 | 99.0 | 70.0 | 89.3 |
| NM 72 | 99.0 | 99.0 | 61.7 | 86.6 |
| NMS 4 | 99.0 | 98.7 | 56.7 | 84.8 |
| Numex-Sahara | 99.0 | 99.0 | 51,7 | 83.2 |
| NMS 2 | 99.0 | 99.0 | 50.0 | 82.7 |
| FB-119 | 99.0 | 98.7 | 48.3 | 82.0 |
| NMS 3 | 99.0 | 99.0 | 45.0 | 81.0 |
| MSB-30 | 99.0 | 94.3 | 46.7 | 80.0 |
| Texturf 10 | 99.0 | 98.7 | 28.3 | 75.3 |
| NM 375 | 99.0 | 99.0 | 26.7 | 74.9 |
| Tifway II | 99.0 | 99.0 | 23.3 | 73.8 |
| MSB-10 | 99.0 | 99.0 | 21.7 | 73.2 |
| Tifway | 99.0 | 94.0 | 18.3 | 70.4 |
| NM 43 | 99.0 | 99.0 | 10.0 | 69.3 |
| MAV-20 | 99.0 | 99.0 | 8.3 | 68.8 |
| Tifgreen | 99.0 | 99.0 | 8.3 | 68.8 |
| Midlawn (A-22) | 99.0 | 97.7 | 0.0 | 65.6 |
| RS-1 | 99.0 | 96.0 | 1.7 | 65.6 |
| A-29 | 99.0 | 96.0 | 0.0 | 65.0 |
| Tufcote | 89.3 | 99.0 | 0.0 | 62.8 |
| Guymon | 97.7 | 76.7 | 13.3 | 62.6 |
| Vamont | 86.0 | 81.3 | 0.0 | 55.3 |
| Midiron | 99.0 | 67.0 | 0.0 | 55.3 |
| Midfield (E-29) | 99.0 | 59.7 | 0.0 | 52.9 |
| LSD VALUE | 8.6 | 24.6 | 23.9 | 11.8 |

[1]To determine statistical differences among entries, subtract one entry's mean from another. Statistical differences occur when this value is larger than the corresponding LSD value (LSD 0.05).

TABLE 6

Genetic Color Ratings of Bermudagrass Cultivars, 1990[1]

| | Genetic Color Ratings (1–9, 9 = dark green) | | | | | | |
|---|---|---|---|---|---|---|---|
| Bermuda clone | AR | AZ | CA2 | CA3 | LA | TX | Mean |
| Tifway II | 7.3 | 7.3 | 8.0 | 8.0 | 8.7 | 9.0 | 8.1 |
| Tifway | 7.7 | 7.3 | 8.0 | 7.7 | 8.7 | 8.0 | 7.9 |
| NM 375 | 7.0 | 7.3 | 7.3 | 8.0 | 9.0 | 8.3 | 7.8 |
| MSB-10 | 7.3 | 7.0 | 8.0 | 8.0 | 8.0 | 7.7 | 7.7 |
| NM 507 | 6.7 | 8.0 | 7.7 | 7.0 | 8.3 | 8.0 | 7.6 |
| MSB-30 | 7.3 | 8.0 | 7.0 | 6.3 | 9.0 | 8.0 | 7.6 |
| NM 471 | 6.3 | 7.7 | 7.7 | 7.7 | 8.0 | 8.0 | 7.6 |
| Tufcote | 6.7 | 6.7 | 6.7 | 6.7 | 7.7 | 8.3 | 7.1 |
| NMS 3 | 5.7 | 7.0 | 7.0 | 6.7 | 8.0 | 8.0 | 7.1 |
| Texturf 10 | 6.7 | 6.7 | 7.0 | 6.3 | 7.7 | 8.0 | 7.1 |
| Midiron | 4.0 | 6.7 | 7.7 | 8.3 | 7.3 | 8.0 | 7.0 |
| NMS 4 | 6.3 | 6.3 | 6.7 | 6.7 | 8.3 | 7.7 | 7.0 |
| A-29 | 6.0 | 6.0 | 7.3 | 7.0 | 7.0 | 7.3 | 6.8 |
| Midlawn (A-22) | 5.7 | 5.3 | 6.7 | 7.0 | 7.7 | 8.0 | 6.7 |
| MSB-20 | 6.3 | 6.7 | 6.7 | 6.7 | 7.0 | 6.7 | 6.7 |
| Tifgreen | 6.3 | 6.3 | 6.7 | 6.3 | 7.0 | 7.3 | 6.7 |
| NM 72 | 5.3 | 7.0 | 6.7 | 6.0 | 7.3 | 7.3 | 6.6 |
| Midfield (E-29) | 5.3 | 5.7 | 7.0 | 6.7 | 6.3 | 8.0 | 6.5 |
| FB-119 | 5.3 | 6.3 | 6.7 | 6.3 | 7.3 | 7.0 | 6.5 |
| Guymon | 4.7 | 6.0 | 6.7 | 7.0 | 7.3 | 7.3 | 6.5 |
| CT-23 | 5.3 | 6.0 | 6.7 | 6.7 | 7.0 | 7.0 | 6.4 |
| NM 43 | 5.7 | 6.3 | 6.0 | 5.7 | 8.0 | 6.3 | 6.3 |
| Numex-Sahara | 5.3 | 5.3 | 5.7 | 5.7 | 8.0 | 7.7 | 6.3 |
| NMS 2 | 5.3 | 5.3 | 6.0 | 5.7 | 7.0 | 7.3 | 6.1 |
| Vamont | 5.0 | 5.3 | 6.7 | 6.0 | 7.3 | 6.3 | 6.1 |
| RS-1 | 4.3 | 5.7 | 7.0 | 6.0 | 7.0 | 6.3 | 6.1 |

TABLE 6-continued

Genetic Color Ratings of Bermudagrass Cultivars, 1990[1]

| Bermuda clone | Genetic Color Ratings (1-9, 9 = dark green) | | | | | | |
|---|---|---|---|---|---|---|---|
| | AR | AZ | CA2 | CA3 | LA | TX | Mean |
| NMJS 14 | 4.7 | 4.7 | 6.3 | 5.0 | 7.0 | 7.3 | 5.8 |
| AZ Common | 5.0 | 4.0 | 5.7 | 5.7 | 7.3 | 7.0 | 5.8 |
| LSD VALUE | 1.6 | 1.0 | 0.7 | 0.9 | 0.7 | 0.8 | 0.4 |

[1]To determine statistical differences among entries, subtract one entry's mean from another. Statistical differences occur when this value is larger than the corresponding LSD value (LSD 0.05).

TABLE 7

Leaf Texture Ratings of Bermudagrass Cultivars, 1990[1]

| Bermuda clone | Leaf Texture Ratings (1-9, 9 = very fine) | | | |
|---|---|---|---|---|
| | AR1 | AZ1 | LA1 | Mean |
| MSB-20 | 8.7 | 8.0 | 9.0 | 8.6 |
| Tifway II | 8.3 | 8.0 | 9.0 | 8.4 |
| MSB-10 | 8.3 | 8.0 | 8.7 | 8.3 |
| NM 43 | 7.7 | 8.0 | 8.7 | 8.1 |
| Tifway | 7.7 | 8.0 | 8.7 | 8.1 |
| Tifgreen | 8.3 | 7.3 | 8.0 | 7.9 |
| Midlawn (A-22) | 7.3 | 8.0 | 8.0 | 7.8 |
| CT-23 | 6.3 | 7.7 | 8.3 | 7.4 |
| NM 471 | 6.0 | 7.0 | 8.3 | 7.1 |
| NM 507 | 6.0 | 7.0 | 8.0 | 7.0 |
| Tufcote | 7.0 | 6.3 | 7.7 | 7.0 |
| NM 72 | 6.0 | 7.0 | 7.3 | 6.8 |
| NMS 3 | 6.3 | 7.0 | 7.0 | 6.8 |
| NMS 4 | 6.0 | 7.0 | 7.0 | 6.7 |
| A-29 | 6.0 | 6.7 | 7.0 | 6.6 |
| FB-119 | 5.7 | 7.0 | 7.0 | 6.6 |
| MSB-30 | 6.0 | 6.7 | 7.0 | 6.6 |
| NM 375 | 6.0 | 6.7 | 7.0 | 6.6 |
| Midron | 6.3 | 6.3 | 7.0 | 6.6 |
| Texturf 10 | 5.3 | 6.3 | 7.7 | 6.4 |
| Midfield (E-29) | 6.3 | 6.3 | 6.0 | 6.2 |
| Numex-Sahara | 5.0 | 6.0 | 7.0 | 6.0 |
| AZ Common | 6.3 | 5.3 | 6.0 | 5.9 |
| NMS 2 | 4.7 | 5.7 | 6.3 | 5.6 |
| RS-1 | 4.7 | 6.0 | 6.0 | 5.6 |
| Vamont | 4.7 | 5.7 | 5.3 | 5.2 |
| NMS 14 | 4.3 | 5.3 | 5.7 | 5.1 |
| Guymon | 3.3 | 5.7 | 5.3 | 4.8 |
| LSD VALUE | 1.2 | 0.7 | 0.6 | 0.5 |

[1]To determine statistical differences among entries, subtract one entry's mean from another. Statistical differences occur when this value is larger than the corresponding LSD value (LSD 0.05).

TABLE 8

Summer Density Ratings of Bermudagrass Cultivars, 1990[1]

| Bermuda clone | Density Ratings (1-9, 9= maximum density) | |
|---|---|---|
| | AR | Mean |
| MSB-20 | 9.0 | 9.0 |
| Tifway | 9.0 | 9.0 |
| Tifway II | 9.0 | 9.0 |

TABLE 8-continued

Summer Density Ratings of Bermudagrass Cultivars, 1990[1]

| Bermuda clone | Density Ratings (1-9, 9= maximum density) | |
|---|---|---|
| | AR | Mean |
| MSB-10 | 8.7 | 8.7 |
| Tufcote | 8.0 | 8.0 |
| Midlawn (A-22) | 7.7 | 7.7 |
| NM 375 | 7.7 | 7.7 |
| NM 43 | 7.7 | 7.7 |
| NM 471 | 7.7 | 7.7 |
| NM 507 | 7.7 | 7.7 |
| Texturf 10 | 7.7 | 7.7 |
| Tifgreen | 7.7 | 7.7 |
| A-29 | 7.3 | 7.3 |
| FB-119 | 7.3 | 7.3 |
| MSB-30 | 7.0 | 7.0 |
| NM 72 | 7.0 | 7.0 |
| Midfield (E-29) | 6.7 | 6.7 |
| Midiron | 6.7 | 6.7 |
| NMS 3 | 6.7 | 6.7 |
| NMS 4 | 6.7 | 6.7 |
| RS-1 | 6.7 | 6.7 |
| CT-23 | 6.3 | 6.3 |
| AZ Common | 5.7 | 5.7 |
| NMS 2 | 5.7 | 5.7 |
| Vamont | 5.7 | 5.7 |
| Numex-Sahara | 5.0 | 5.0 |
| NMS 14 | 5.0 | 5.0 |
| Guymon | 4.3 | 4.3 |
| LSD VALUE | 1.1 | 1.1 |

[1]To determine statistical differences among entries, subtract one entry's mean from another. Statistical differences occur when this value is larger than the corresponding LSD value (LSD 0.05).

TABLE 9

Evaluation of Bermudagrass Clones at the Horticulture Research Center, Wichita, KS for Susceptibility to Spring Dead Spot

| Bermuda clone[1] | Number of Spots | % Area w/Spots | % Kill in Spots | Total Plot Quality[2] |
|---|---|---|---|---|
| Midiron | 2.0 | 4.0 | 26.7 | 8.7 |
| Midlawn (A-22) | 1.3 | 6.2 | 21.7 | 9.0 |
| Midfield (E-29) | 2.3 | 7.8 | 26.7 | 8.0 |
| A-29 | 2.3 | 12.9 | 33.3 | 8.0 |
| Guymon | 2.7 | 10.0 | 70.0 | 6.0 |
| Midway | 2.0 | 11.5 | 43.3 | 7.0 |
| RS-1 | 3.3 | 20.6 | 70.0 | 6.3 |
| Texturf 10 | 3.0 | 24.7 | 96.7 | 5.7 |
| Vamont | 3.3 | 26.1 | 95.0 | 4.6 |
| Sunturf | 3.3 | 32.7 | 90.0 | 4.7 |
| Tifgreen | 4.0 | 36.11 | 98.3 | 4.0 |
| LSD (P = 0.05) | 0.3 | 14.7 | 17.0 | 1.4 |

[1]Other clones in test with complete winter kill in at least two of the three replicated plot included CT-23, NM 43, NM72, NM375, NM 471, NM507, MSB-10, MSB-20, MSB-30, Tufcote, Tifway, Tifway II, NMS1, NMS3, NMS4, NMS14, Arizona Common, and FB119.

[2]Plot quality rating where 0 = complete kill of plot, and 9 = 90% or better coverage of plot.

t,180

Having thus described the invention, the following is claimed as new and desired to be secured by Letters Patent:

1. A new and distinct variety of Bermudagrass as shown and described.

* * * * *